United States Patent [19]

Din et al.

[11] Patent Number: 5,782,796
[45] Date of Patent: Jul. 21, 1998

[54] FOLDABLE DIALYSIS UNIT WITH INTEGRAL PUMP AND A METHOD FOR PERFORMING SOLUTION EXCHANGE

[75] Inventors: Shahid Din, Clearwater; Greg Worsnick, Tampa, both of Fla.

[73] Assignee: Baxter International Inc., Deerfield, Ill.

[21] Appl. No.: 387,050

[22] Filed: Feb. 10, 1995

[51] Int. Cl.$^6$ .............................................. A61M 1/00
[52] U.S. Cl. .............................................. 604/29; 604/27
[58] Field of Search ....................... 604/27, 29, 30, 604/34, 33, 67, 80, 81

[56] References Cited

U.S. PATENT DOCUMENTS

| | | | |
|---|---|---|---|
| 3,552,393 | 1/1971 | Willgerodt | 604/27 X |
| 3,620,215 | 11/1971 | Tysk | 604/29 |
| 4,003,536 | 1/1977 | Sekerich . | |
| 4,096,859 | 6/1978 | Agarwal et al. | 604/29 X |
| 4,239,041 | 12/1980 | Popovich et al. | 604/29 X |
| 4,290,625 | 9/1981 | Barriere . | |
| 4,412,917 | 11/1983 | Ahjopalo | 604/29 X |
| 4,560,472 | 12/1985 | Branzow et al. | 604/29 X |
| 4,769,134 | 9/1988 | Allan et al. . | |
| 5,141,492 | 8/1992 | Dadson et al. | 604/29 X |
| 5,141,493 | 8/1992 | Jacobsen et al. | 604/29 |
| 5,338,194 | 8/1994 | Strohmaier | 604/27 X |
| 5,401,238 | 3/1995 | Pirazzoli . | |
| 5,438,510 | 8/1995 | Bryant et al. . | |
| 5,445,610 | 8/1995 | Evert . | |
| 5,472,614 | 12/1995 | Rossi . | |
| 5,474,683 | 12/1995 | Bryant et al. . | |

FOREIGN PATENT DOCUMENTS

| | | |
|---|---|---|
| 0 028 371 A1 | 5/1981 | European Pat. Off. . |
| GN 2 248 106 | 3/1992 | United Kingdom . |
| WO88/07384 | 10/1988 | WIPO . |
| WO94/11093 | 5/1994 | WIPO . |

*Primary Examiner*—Robert A. Hafer
*Assistant Examiner*—Benjamin Koo
*Attorney, Agent, or Firm*—Charles R. Mattenson; Thomas S. Borecki; Robert M. Barrett

[57] ABSTRACT

A system and a method are provided to effect solution exchange particularly for a patient requiring peritoneal dialysis. The system includes a device (1) that is portable and particularly adaptable for patients requiring a night time exchange or an additional exchange. The device (1) includes an operator-touch control panel (10) operatively connected to a pouch (26) with an incorporated heater (12). The pouch (26) holds a solution bag (18) and may be selectively opened and closed by a cover (28). A drain tray (30) holds a drain bag (20) and has a scale (14) incorporated therein. The pouch (26) is connected to the control panel (10) by an upper arm (38), and the drain tray (30) is connected to the control panel (10) by a lower arm (42). The device (1) may be collapsed by releasing the upper arm (38) and the lower arm (42) such that the system (1) lays in a substantially flat arrangement when not in use.

49 Claims, 8 Drawing Sheets

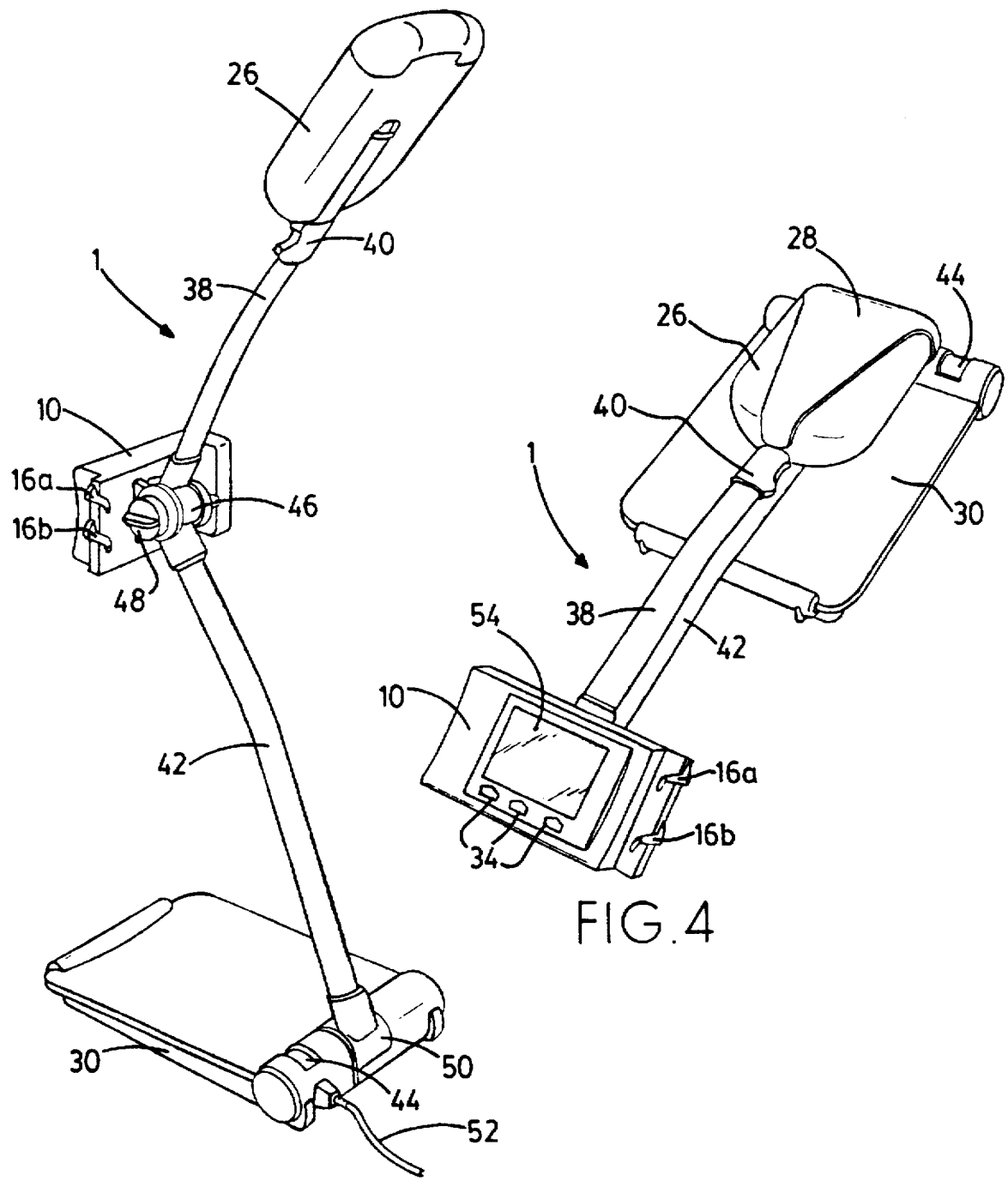

5,782,796

FOLDABLE DIALYSIS UNIT WITH INTEGRAL PUMP AND A METHOD FOR PERFORMING SOLUTION EXCHANGE

BACKGROUND OF THE INVENTION

The present invention generally relates to a pumping system. More specifically, the present invention relates to a system and a method for pumping fluid, particularly for peritoneal dialysis.

As is well known, peritoneal dialysis is a procedure for removing toxic substances and metabolites normally excreted by the kidneys and for aiding in the regulation of fluid and electrolyte balance. Peritoneal dialysis is accomplished by instilling peritoneal dialysis fluid through a conduit into a peritoneal cavity of an individual. The instilled peritoneal dialysis fluid contains ionic concentrations of electrolytes that are similar to those in the physiological extracellular fluid with the exception of lactate which is present as a bicarbonate precursor.

Fluid and solute transport occur across the peritoneal membrane between the plasma of the patient and the instilled dialysis fluid. These processes result in normalization of plasma electrolyte profiles. Toxic substances and metabolites present in high concentrations in the blood cross the peritoneal membrane into the dialyzing fluid. Dextrose, in varying concentrations, is used in the dialyzing fluid to produce a solution hyperosmolar to the plasma thus creating an osmotic gradient that facilitates fluid removal from the patient's plasma into the peritoneal cavity.

After a period of time (dwell time), the spent or used dialysis fluid is removed from the peritoneal cavity. Peritoneal dialysis is required for patients with acute or chronic renal failure when non-dialytic medical therapy is judged to be inadequate.

One form of peritoneal dialysis, continuous ambulatory peritoneal dialysis (CAPD) involves maintaining dialysis solution in constant contact with the peritoneal membrane throughout the entire day. To conduct CAPD, the patient manually drains spent dialysate and manually instills new dialysate performing a number of necessary manipulations during the procedure. CAPD relies on gravity to move fluid in and out of the peritoneal cavity. The peritoneal dialysis solution is changed approximately three to five times per day and typically four exchanges per day. Usually, three of these exchanges include dwell times of four to six hours while an overnight exchange may include a dwell time of eight to ten hours.

During the long, overnight dwell period, the efficiency of fluid removal may be reduced if the osmotic gradient is lost due to uptake of dextrose into the patient over time. Also, the ability of the dialysis fluid to promote clearance of uremic toxins is reduced once the concentration of the toxin in the dialysis fluid reaches the plasma concentration of the analyte. Thus, removing spent fluid and replacing it with fresh dialysis solution (the addition of a fifth peritoneal dialysis exchange) during the overnight period may be helpful to patients requiring additional fluid or toxin removal.

The present invention, therefore, provides a system and a method to satisfy a need of patients requiring a fifth peritoneal dialysis exchange (during sleep) or for patients who desire a more convenient method to perform four exchanges per day by skipping one daytime exchange. The present invention, therefore, provides a system and a method for a night exchange that aids in removing peritoneal dialysis solution into and out of the patient and allows the patient additional freedom of movement during the procedure.

SUMMARY OF THE INVENTION

The present invention provides a system and a method for automatic control of exchanged solutions, particularly for treatment of renal failure patients undergoing peritoneal dialysis. The system provides a device, particularly suitable for patients requiring a fifth dialysate solution exchange. The device automatically drains spent fluid from the peritoneum and fills with a prescribed volume of peritoneal dialysis fluid warmed to body temperature.

To this end, in an embodiment, the present invention provides a system for controlling fluid flow. The system has a holder capable of holding a first container having a first solution therein. A processor unit has a means for controlling flow connected to the holder wherein the means for controlling flow is capable of controlling flow of the first solution from the first container in the holder. A tray is provided capable of holding a second container wherein the means for controlling flow is capable of controlling flow of a second solution to the second container.

In an embodiment, a heater is incorporated in the holder capable of heating the first solution in the first container in the holder.

In an embodiment, a scale is incorporated in the tray capable of weighing the second container placed on the tray.

In an embodiment, the system includes a fill valve controlling flow of the first solution from the first container.

In an embodiment, the system includes a drain valve controlling flow of the second solution to the second container.

In an embodiment, an arm connects the holder to the processor unit.

In an embodiment, an arm connects the processor unit to the tray.

In an embodiment, a display is operatively connected to the processor unit.

In an embodiment, an input means is operatively connected to the processor unit.

In an embodiment, means are provided for effecting structural relationships between the holder and the processor unit.

In an embodiment, a cover is connected to the holder to substantially enclose the first container in the holder.

In an embodiment, a power switch is operatively connected to the tray to activate the system.

In an embodiment, means are provided to alter position of the processor unit.

In an embodiment, means are provided to release the holder, the processor unit and the tray to orient in a non-operable position.

In an embodiment, an audible means is provided operatively connected to the processor unit capable of producing an audible signal.

In an embodiment, an auxiliary processor is provided in the tray operatively connected to the processor unit.

In an embodiment, a real time clock is operatively connected to the processor unit.

In an embodiment, a programmable timing means is operatively connected to the processor unit to control activation of the system.

In an embodiment, operator-actuated keys are provided to control programming of the processor unit. The operator-actuated keys are modifiable by the processor unit.

In an embodiment, the means for controlling flow of the system is a pneumatic pump.

In an embodiment, sensing means are provided for detecting temperature of the first solution in the container.

In an embodiment, a plurality of strain gauges are constructed and arranged with the tray capable of measuring weight of the second container on the tray.

In another embodiment of the present invention, a method is provided for controlling fluid flow. The method comprises the steps of: providing a holder capable of holding a first container having a first solution without hanging the first container; providing a tray capable of holding a second container having a second solution without hanging the second container, the first container remotely situated from the second container; and controlling flow of the first solution from the first container and the flow of the second solution to the second container.

In an embodiment, the method further comprises the step of weighing the second solution in the second container without removing the second container.

In an embodiment, the method further comprises the step of heating the first solution in the holder.

In an embodiment, the method further comprises the step of selectively enclosing the first container in the holder.

In an embodiment, the method further comprises the step of sensing temperature of the first solution in the first container.

In an embodiment, the method further comprises the step of controlling draining of the first container and the filling of the second container.

In an embodiment, the method further comprises the step of draining the first container only after weighing the second container.

In an embodiment, the method further comprises the step of folding the holder and the tray into a second position not suitable for use.

In an embodiment, the method further comprises the step of providing a display indicative of performed functions.

In an embodiment, the method further comprises the step of providing a cover to selectively enclose the first container in the holder.

In another embodiment of the present invention, a bag holder is provided having a container selectively openable to hold a bag therein. A cover encloses the container in the bag holder wherein the cover is hinged to the container. A heating element is incorporated in the container capable of heating a solution in the bag.

In an embodiment, the bag holder further has an opening in the container through which an extension of the cover is inserted wherein the cover is pivotable at the opening.

In an embodiment, the heating element is a film etched in the container.

In an embodiment, a sensor is incorporated with the heating element to detect temperature variations of the solution in the bag.

In an embodiment, the container of the bag holder is insulated.

In another embodiment of the present invention, a portable peritoneal dialysis exchange system is provided. The system has a drain tray capable of holding a drain bag without hanging the drain bag. A pouch is capable of holding a solution bag without hanging the solution bag. A collapsible linkage connects the drain tray to the pouch, and a processor having a flow control means is operatively connected to the drain bag and the solution bag to control flow of fluid to the drain bag from a patient and from the solution bag to the patient.

In an embodiment, the system has a scale incorporated in the drain tray to measure weight of the drain bag.

In an embodiment, the system has a heating means incorporated in the pouch to effect heating of the solution bag and its contents.

In an embodiment, valves are associated with the processor to assist the flow control means to control flow of fluids.

In an embodiment, the processor of the system is constructed and arranged between the drain tray and the pouch wherein the pouch gravitationally feeds fluid from the solution bag toward the processor.

In an embodiment, a display is associated with the processor displaying functions of the processor.

In an embodiment, keys are associated with the processor to control programmable functions of the processor.

In an embodiment, a cover is constructed and arranged to selectively open and close the pouch.

In an embodiment, means for adjusting orientation of the processor without affecting the orientation of the pouch is provided.

In an embodiment, a handle is constructed and arranged on the linkage to selectively effect collapse of the linkage.

It is, therefore, an advantage of the present invention to provide a system and a method for solution exchange that is simple to use.

Yet another advantage of the present invention is to provide a system and a method for solution exchange that is convenient to use.

A further advantage of the present invention is to provide a system and a method for solution exchange that is cost-effective to use.

A still further advantage of the present invention is to provide a system and a method for solution exchange that requires use of a portable device.

Moreover, an advantage of the present invention is to provide a system and a method for solution exchange particularly suitable for patients requiring peritoneal dialysis.

And, another advantage of the present invention is to provide a system and a method for solution exchange that may be performed during the night time and/or while a patient is sleeping.

A further advantage of the present invention is to provide a system and a method for solution exchange that is programmable.

A still further advantage of the present invention is to provide a system and a method for solution exchange that is compact so as to be easily stowed.

And, another advantage of the present invention is to provide a system and a method for solution exchange capable of heating a solution using minimal power and minimizing heat loss.

Moreover, an advantage of the present invention is to provide a system and a method for solution exchange that prevents filling of one solution prior to draining of a second solution.

Another advantage of the present invention is to provide a system and a method for solution exchange that is safe to use.

Yet another advantage of the present invention is to provide a system and a method for solution exchange that provides suitable alarm conditions to notify a patient of conditions or failure in the system.

BRIEF DESCRIPTION OF THE DRAWINGS

FIG. 3 illustrates a rear perspective view of an embodiment of the system of the present invention.

FIG. 4 illustrates a perspective view of the system of the present invention in its collapsed or folded position.

DETAILED DESCRIPTION OF THE PRESENTLY PREFERRED EMBODIMENTS

Figures 1, 2:
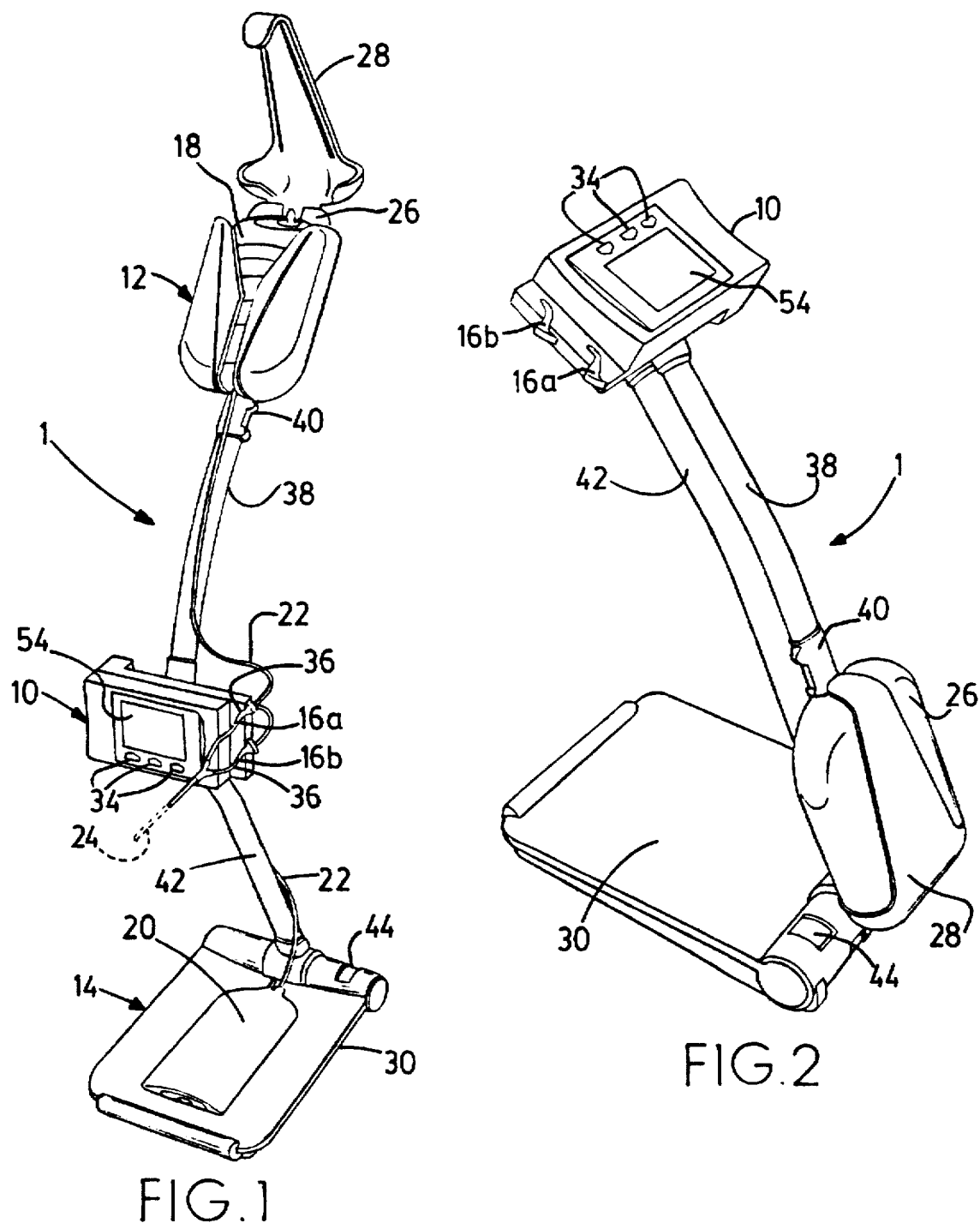
FIG. 1 illustrates a front perspective view of an embodiment of the system of the present invention.
FIG. 2 illustrates a perspective view with one arm folded up in an embodiment of the system of the preset invention.

The present invention provides a system for automatic control of dialysate solution exchange in treatment of chronic renal failure patients undergoing peritoneal dialysis. The system includes a machine that automatically drains spent fluid from the peritoneum then fills the same with a prescribed volume of peritoneal dialysis fluid warmed to body temperature. The device fills the need for patients who require a peritoneal dialysis exchange, such as a fifth exchange, night time exchange, or those patients requiring a more convenient time and method for performing four exchanges by skipping one day time exchange.

The system is designed for use with a peritoneal dialysis solution container, such as, for example, a Dianeal™ peritoneal dialysis solution in an Ultrabag™ container manufactured and sold by Baxter Healthcare Corporation of Deerfield, Ill. Such a container consists of a solution bag, administration tubing and a drain bag. Other similar twin bag systems may be implemented with the system of the present invention.

A sterile fluid path of the twin bag transfers the peritoneal dialysis solution to and from a patient during the dialysis treatment. An extension line may further be provided to lengthen the fluid path allowing the patient more freedom of movement once connected to the system. Such an extension line is typically a single use product.

Referring now to the drawings wherein like numerals refer to like parts, an embodiment of an exchange system of the present invention is generally designated at 1. The system 1 includes four principal components: an operator touch control panel 10, an insulated heater 12 incorporated in a pouch 26, a scale 14 incorporated in a drain tray 30 and at least two automated valves 16a, 16b.

As illustrated in FIG. 1, a solution bag 18 is provided within the pouch 26 including the insulated heater 12, and a drain bag 20 is laid on the drain tray 30 including the scale 14. Administration tubing 22 connects the drain bag 20 and the solution bag 18 with the system 1 and the automated valves 16a, 16a. An extension line tubing 24 connects to the administration tubing 22 and extends to a patient 2 (as shown in FIG. 5) subjected to the peritoneal dialysis procedure.

Figure 5:
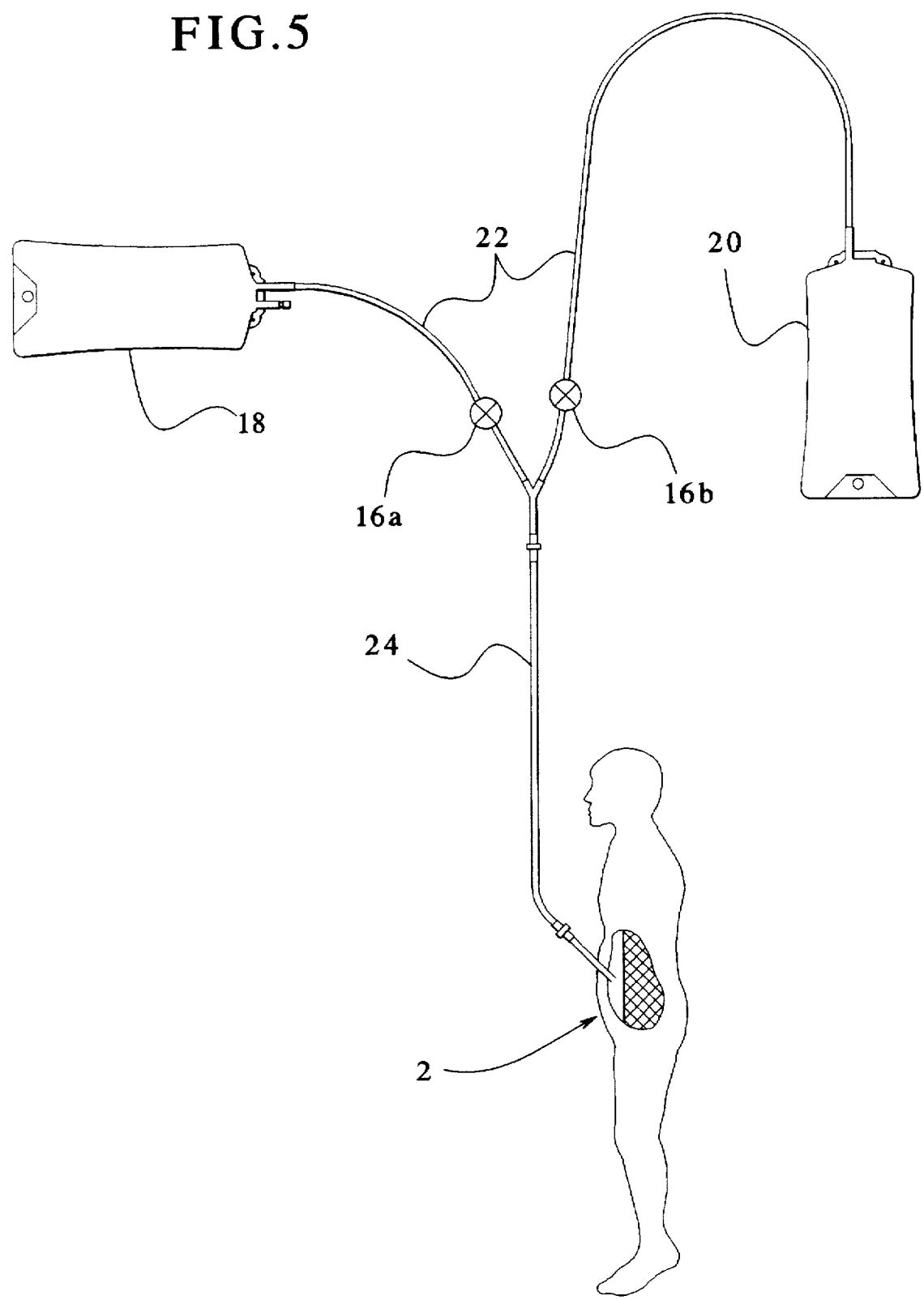
FIG. 5 illustrates an environmental view of the general flow requirements of solutions to and from a patient requiring peritoneal dialysis.

Referring now to FIG. 5, a fluid flow diagram demonstrating how the system 1 of the present invention cycles fluid into and out of a patient 2 is shown. To this end, the system 1 consists of the two automated valves 1; one valve 16a is a fill valve between the solution bag 18 and the extension line 24 and the other valve 16a is a drain valve between the extension line tubing 24 and the drain bag 20. The administration tubing 22 connects the valves 16a and 16a to the solution bag 18 and the drain bag 20, respectively.

Referring again to FIGS. 1-4, the exchange system 1 generally consists of a collapsible S-shaped pole with three distinct areas: a top portion, a bottom portion and a middle portion. The top portion of the exchange system 1 includes the insulated heater 12 incorporated in a shell of the pouch 26 for holding the solution bag 18. The pouch 26 is insulated and includes the heater 12 designed to slowly warm the solution bag 18 and the solution therein to a temperature approximately equal to body temperature. The solution bag 18 is loaded into the pouch 26 with the administration tubing 22 exiting a bottom end of the pouch 26. A cover 28 encloses the pouch 26 holding the solution bag 18. The cover 28 may be folded to enclose the pouch 26 as illustrated in FIGS. 2 and 4.

The bottom portion of the exchange system includes the drain tray 30 with the scale 14 incorporated therein. The scale 14 is capable of measuring a weight of the fluid drained into the drain bag 18 that is fed from the administration tubing 22 into the drain bag 20. The drain bag 20 may be placed on the drain tray 30 in any position to determine the weight of the drain bag 20 using the incorporated scale 14. As illustrated in FIG. 1, the drain bag 20 is centrally located on the drain tray 30.

Finally, the middle portion includes the operator touch control panel 10 and the automated clamps or valves 16a, 16a. The operator touch control panel 10, in a preferred embodiment, is an LCD display 54 provided with various sized fonts and icons making the exchange system 1 easy-to-use and flexible for various language formats. To this end, three keys 34 are provided allowing input of information.

Two notched areas 36 are also provided to accept the administration tubing 22. The notched area 36 includes the valve 16a that controls fluid flow from the solution bag 18 through the extension line tubing 24 and to the patient 2 while the other notched area 36 includes the valve 16a and receives solution from the patient 2 and drains the same to the drain bag 20 on the drain tray 30. Preferably, the administration tubing 22 from the solution bag 18 goes through the top notched area 36 while the bottom notched area 36 receives the administration tubing 22 leading to the drain bag 20.

Connecting the top portion to the middle portion is an upper arm 38. A release handle 40 is provided along a length of the upper arm. The release handle 40 includes a lever requiring manipulation to fold the exchange system 1 for storage or transport. A lower arm 42 connects the middle portion with the lower portion. A power switch 44 is preferably provided on the lower portion adjacent the drain tray 30 to activate and deactivate the exchange system 1.

Referring to FIG. 3, the exchange system 1 includes an upper knuckle 46 at the middle portion opposite a face of the operator touch control panel 10. The upper knuckle 46 includes a tilt adjuster 48 that adjusts the view angle of the operator touch control panel 10. The lower knuckle 50 is provided at the lower portion of the exchange system 1 and connects the lower arm 42 to the drain tray 30. The upper knuckle 46 connects the upper arm 38 to the lower arm 42 and also connects the operator touch control panel 10 therebetween. A detachable power cord 52 is connected to the lower portion at the drain tray 30.

Referring now to FIG. 4, the fill valve 16a and the drain valve 16a are shown adjacent the operator touch control panel 10. The fill valve 16a connects to the administration tubing 22 that connects to the solution bag 18. The fill valve 16a controls flow of solution from the solution bag 18 to the patient 2. Similarly, the drain valve 16a is at a location where the drain line is inserted and is capable of controlling the flow of solution from the patient 2 to the drain bag 20 on the drain tray 30.

The operator touch control panel 10 includes the display 54. The display 54 displays information with respect to set-up of the exchange system 1 prior to use. During use, the display 54 displays information with respect to progress of treatment. The control keys 34, in conjunction with the display 54, of the operator touch control panel 10 are used for set-up for treatment.

To use the exchange system 1, a well-lit area with a clean, flat surface is preferred. The exchange system 1 is particularly adaptable for home use, particularly for patients who require an exchange at night. Therefore, a night stand or a table near a bed of the patient is typically a good choice for setting up the system 1. An outlet is further required for plugging in the power cord 52 to provide power to run the exchange system 1.

To operate the exchange system 1, the bag 18 containing a solution, such as Dianeal™, distributed by Baxter Healthcare Corporation of Deerfield, Ill., may be used with a separate or pre-attached set. A prep kit or disconnect cap as well as any other accessories typically required for performing a CAPD exchange are also necessary. An extension set is further required, such as the extension line tubing 24.

The exchange system 1 is typically stored in the position illustrated in FIG. 4. To set up the exchange system 1, the lower arm 42 is raised to the position shown in FIG. 2. The upper arm 38 may then be pulled to unfold the exchange system 1 into an upright position as illustrated in FIGS. 1 and 3. The upper knuckle 46 and the lower knuckle 50 are designed such that the exchange system 1 remains in position and will not collapse prior to full extension of the upper arm 38 and the lower arm 42.

After the exchange system 1 is converted to the position illustrated in FIGS. 1 and 3, the power cord 52 is plugged into a grounded outlet. The solution bag 18 and the drain bag 20 with the fill line and the drain line as part of the administration tubing 22 may then be loaded into the system 1 as illustrated in FIG. 1. The extension line tubing 24 may be attached to the administration tubing 22 for connection to a patient. To this end, the fill line of the administration tubing 22 is pressed onto the fill valve gate at the location of the automated valve 16a. Tubing is inserted into the slots, and the automated fill valve 16a with its gate springs back into its original position. The drain line is similarly inserted into the drain valve 16b.

Prior to initial set-up, the power switch 44 turns on the system and instructions are provided for each step required to set up the system 1. That is, the display, following power-up provides the message "LOAD SET AND ATTACH EXTENSIONS". The display 54 includes a real time clock and a programmable time to activate the exchange. The display 54, following set-up, provides instructions, such as the following: "CONNECT SET, BREAK FRANGIBLES AND VERIFY FLOW". These instructions indicate to the user or administrator that an auto-flush procedure will take place. This initiates fluid flow from the fill bag to the drain. After the flush from the fill bag has been completed, the display 54 will read "OPEN TRANSFER SET". The patient transfer set clamp is then opened.

At this point, fluid from the patient flows from the drain bag. The drain valve 16b then closes after an appropriate flush volume has been detected on the drain tray. Then, the patient can go to bed.

During the night, an exchange takes place at the designated time programmed on the display 54. Therefore, following flushing, the display 54 indicates that the flush is complete ("FLUSH COMPLETE") and further indicates that set-up is complete by providing an appropriate message such as "GOOD NIGHT." At the programmed time, for example, 2:00 a.m., the exchange system 1 opens the drain valve 16b and drains the fluid from the patient's peritoneal cavity into the drain bag 20. After the drain is complete, the system 1 opens the fill valve 16a, and fresh solution flows into the peritoneal cavity. During this time, the display 54 may provide an indication of the amount of fluid in the drain bag 20 by that information sensed and transmitted by the scale 14 incorporated within the drain tray 30.

The following day, the patient 2 can touch any of the keys 34 on the control panel 10, and the display 54 will activate. The patient 2 is then instructed by the display 54 of the operator touch control panel 10 to "CHECK FILL BAG", "ATTACH CLAMPS", and "CLOSE TRANSFER SET AND CAP OFF." Therefore, the patient 2 is required to be attached to clamps and to each line to eliminate spilling during removal and to open a new disconnect cap and to cap off the transfer set. The disposable is then removed and discarded using normal procedures required for CAPD. An "UNLOAD" instruction is then provided, and an indication of the drain volume may be displayed as well.

The exchange system 1 may then be put away by the patient 2 by pressing the release handle 40 and pressing down simultaneously on the upper arm 38. The lower arm 42 simultaneously releases such that the exchange system 1 is forced to the position as illustrated in FIG. 4.

The operator touch control panel 10 allows a user to program a number of therapy parameters. For example, the exchange time, the drain time, the set time, the set date and the previous fill volume may all be programmed. The display 54 provides step-by-step instructions for effecting programming of each parameter using only the three keys 34 adjacent the display 54 on the operator touch control panel 10.

The operator touch control panel 10 may also include an alarm 56 or an audio prompt or other features as required by the system 1. Whenever the exchange system 1 identifies a problem in the system 1, the system 1 may sound an alarm and may immediately stop moving solution. The type of alarm may be displayed. Two basic types of alarms may occur during therapy: an alarm capable of correction by the patient or with minimal assistance prompt and aid or an alarm indicative of system error caused by a problem within the exchange system 1. Following an alarm, the display 54 prompts the patient or user to correct the condition. A number of alarm messages may be displayed on the display 54 and appropriate trouble shooting messages may follow. Examples of such alarm messages include "CHECK DRAIN LINE", "CHECK DRAIN TRAY", "CHECK FILL LINE", "CHECK HEATER BAG", "CHECK PATIENT LINE", "DRAIN NOT COMPLETE" and "SYSTEM ERROR."

The heater 12 incorporated in the insulated pouch 26 of the exchange system 1 is connected at a top end of the upper arm 38 and is provided by an aluminum plate with a resistive heating element and a thermally insulated enclosure to receive the solution bag 18. A thermal circuit interrupting device is mounted on the heater plate and shuts down the heater in the event of a thermal run away condition.

Figure 6A:
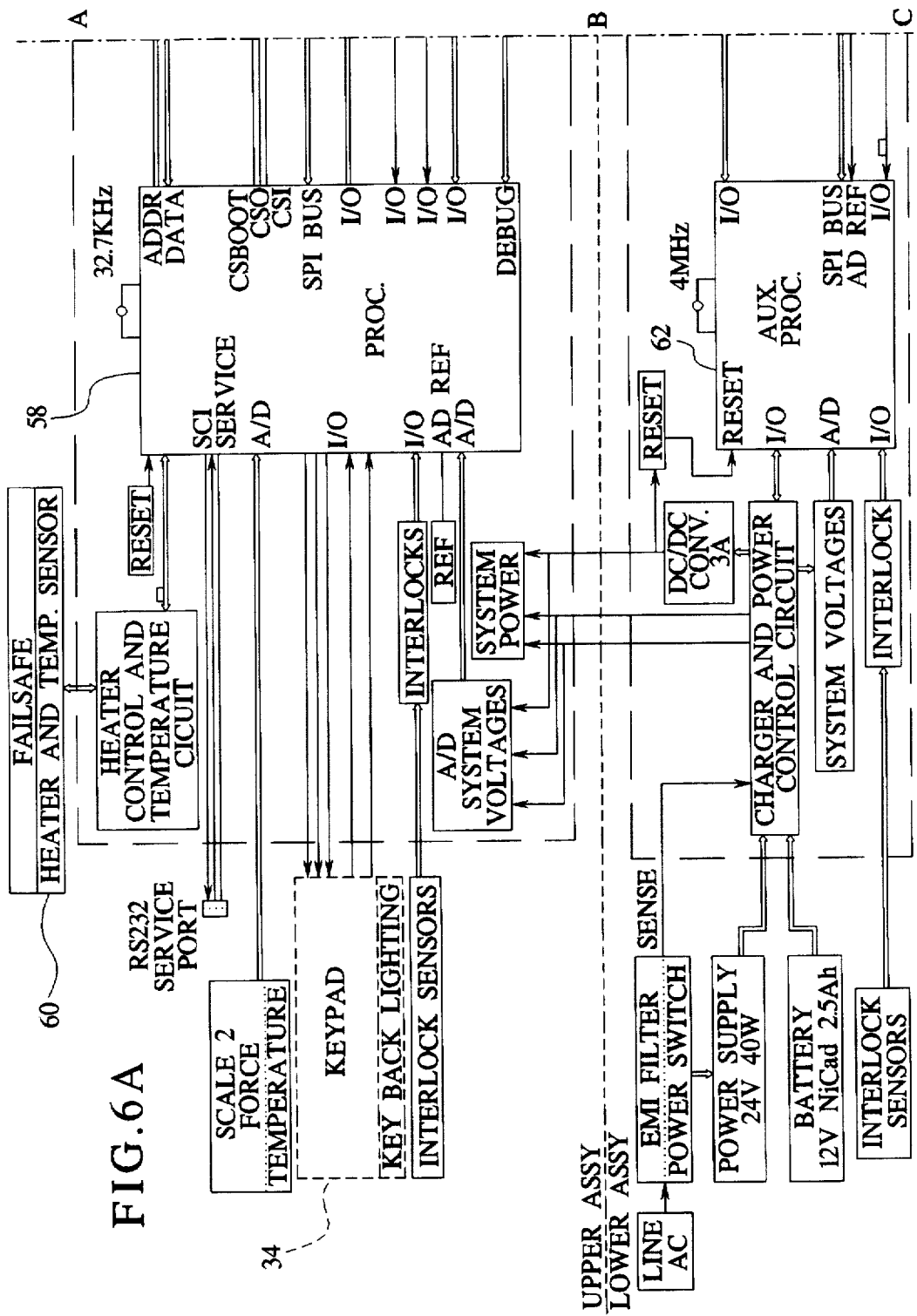
FIG. 6 illustrates a black box diagram of the hardware components in an embodiment of the present invention.
Figure 6B:
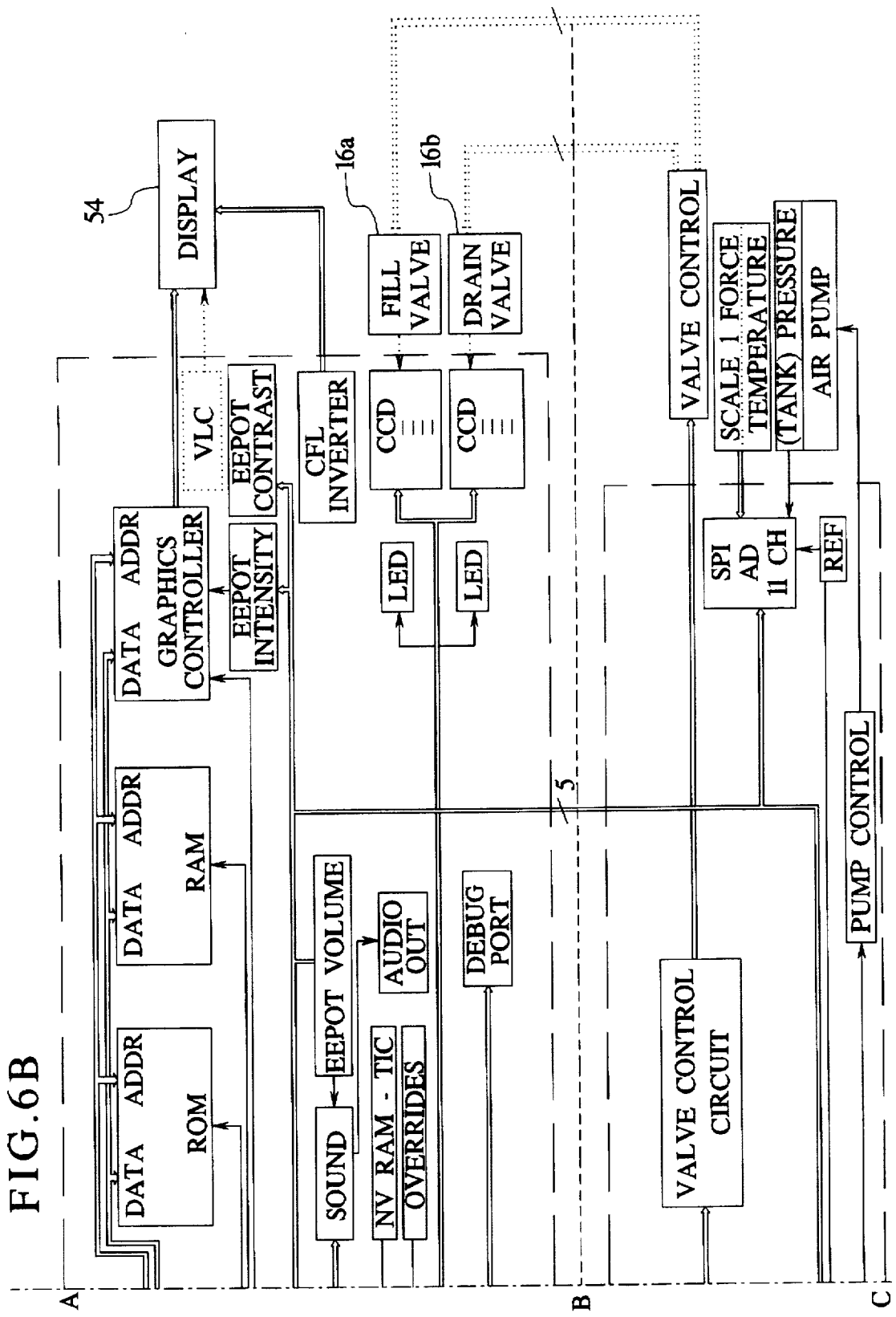

Referring now to FIG. 6, a block diagram of the electronics necessary for operating the exchange system 1 is illustrated. A processor 58 is provided and mounted within the operator touch control panel 10. The processor 58 monitors all inputs to the system 1 and controls the display 54, the valves 16a, 16b, the heater 60, the pump and other subsystems, such as the alarm 56.

An auxiliary processor 62 may be provided and located in the base platform of the drain tray 30. The auxiliary processor 62 is used as a slave device to implement certain control and monitoring functions of components, particularly at the location of the drain tray 30. The primary purpose of the auxiliary processor 62, however, is to minimize the amount of interconnect cabling required between the operator touch control panel 10 and the base portion at the drain tray 30.

Figure 7:
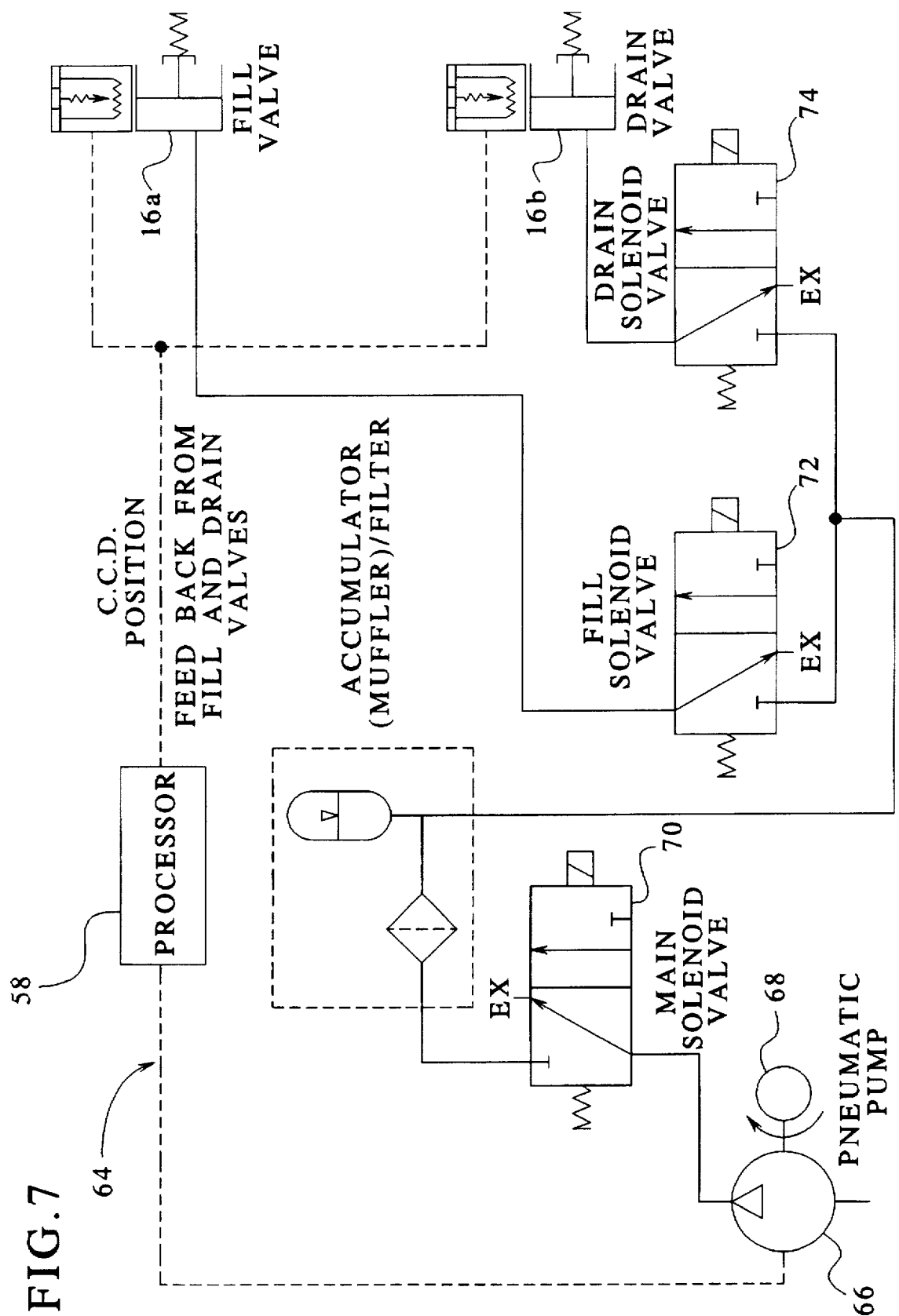
FIG. 7 illustrates a circuit diagram of the pneumatics required for the system in an embodiment of the present invention.

The fill and drain valves 16a and 16b, respectively, operate by a pneumatic system requiring a pneumatic circuit as illustrated in FIG. 7. The pneumatic circuit is generally designated at 64 in FIG. 7 and includes a pneumatic pump 66 driven by a motor 68. The pump 66 is connected to three solenoid-type pneumatic valves 70, 72 and 74. The three solenoid-type valves 70, 72 and 74 are located in the base portion under the drain tray 30 and provide routing of air pressure to the two valves 16a and 16b located in the operator touch control panel 10 via two pneumatic tubes between the base portion and the panel 10.

To open the fill valve 16a, the pneumatic pump 66 is first turned on with the main solenoid valve 70 in the vented position to allow the pump 66 to start-up. Following start-up of the pump 66, the fill solenoid valve 72 and the main solenoid valve 70 are opened. Pressure builds in a pinch valve diaphragm and the valves open. When the valve positions indicate that the valve is open, the main solenoid valve 70 is placed back in the vented position, and the pump 66 is turned off. To close the filled solenoid valve 72, the filled solenoid valve 72 is placed in the vented position.

The drain solenoid valve 74 operates in a similar manner as the fill solenoid valve 72. The valves 16a, 16b are spring-loaded, and the solenoid valves are normally vented when not energized so that the spring will assure that the valves will fail in the closed position.

Figure 8:
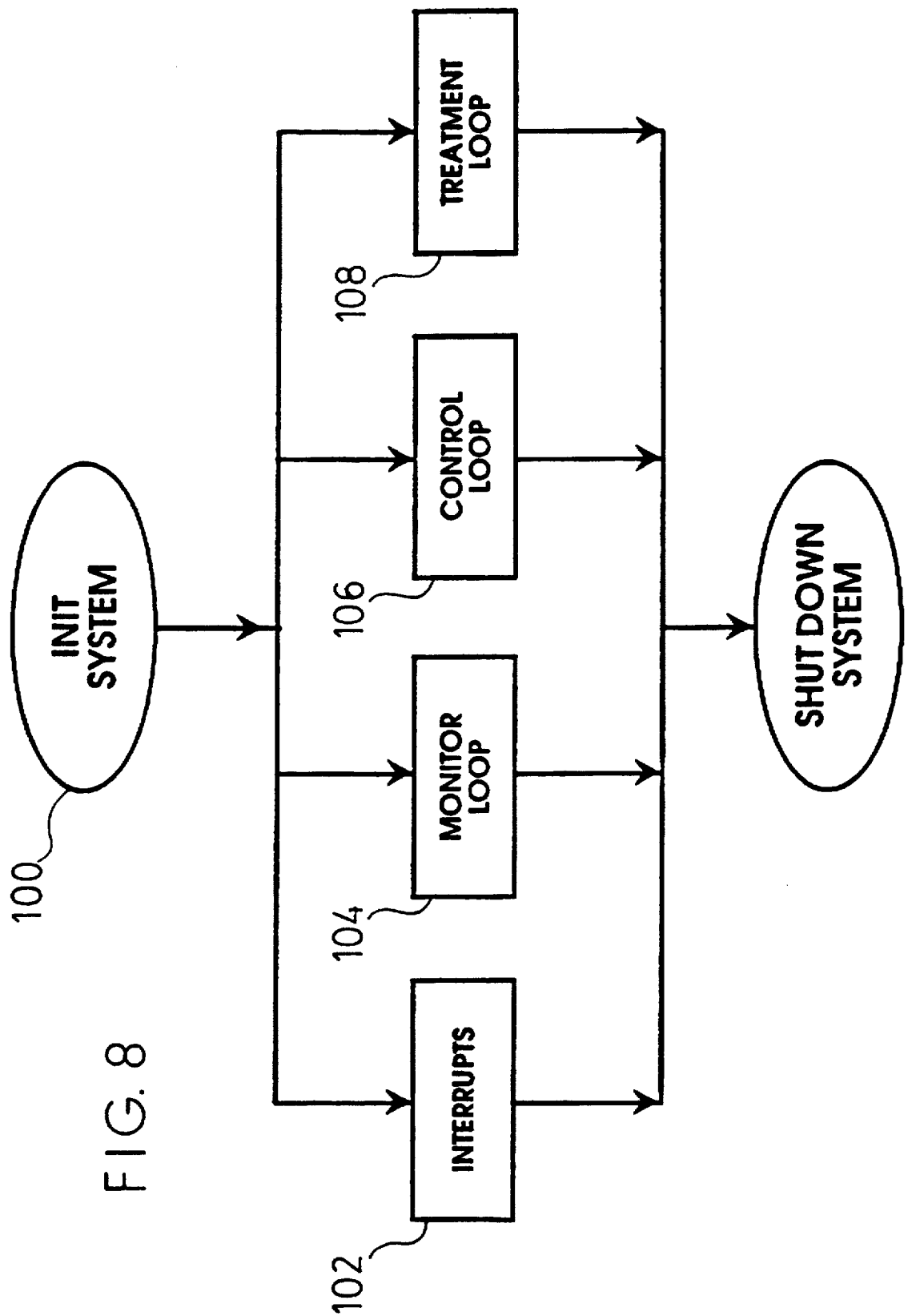
FIG. 8 illustrates a general flow chart of a structure of the main program to operate the system and method of an embodiment of the present invention.

Preferably, the main processor 58 and the auxiliary processor 62 control and monitor all operations of the exchange system 1. The main processor 58 is preferably a master sixteen-bit microcontroller, and the auxiliary processor 62 is preferably a slave eight-bit microcontroller. The software architecture is shown in FIG. 8 after the system 1 is initialized as generally designated at 100, for concurrently running tasks 102, 104, 106 and 108. These tasks include interrupt tasks 102, monitor tasks 104, control tasks 106 and treatment tasks 108.

All tasks in this system can be classified as either control tasks, monitor tasks, or interrupt tasks. Interrupt tasks are operations to effect a change in a physical component such as, for example, the valves, the heater, the pump and/or the display panel. Monitor tasks are operations that read the status of physical components such as temperature, fluid, the position of valves or user keys. Control and monitor tasks are not intertwined as is usually done in single-threaded software. On the contrary, a clear software boundary is defined between control and monitor functions to provide a completely modular and easily verifiable software. The modules communicate with each other with relatively few global variables. Therefore, changes in one module are prevented from adversely propagating to other modules. The interrupt tasks are generated by either external or internal conditions and must be serviced immediately.

The main processor 58 and the auxiliary processor 62 are linked through a serial peripheral interface. The master-slave protocol consists of a data-in, data-out, data-clock and a slave-select line. The main processor 58 acts as the master and orchestrates the entire communication. By selecting the auxiliary processor 62 as the slave, the two processors 58,62 exchange eight bits of data. For master-to-slave, this is a command byte; for slave-to-master, this is an input data byte. If a longer command or data transfer is necessary, a simple multi-byte protocol may be used.

To ensure data integrity, additional safeguards are built on top of the basic serial peripheral interface protocol. Periodically, the two processors 58,62 exchange time stamps so that if, for some reason, either processor 58 or 62 is not performing as required, the other processor detects the same and an orderly fault recovery can be attempted.

As previously discussed, the operator touch control panel 10 includes the operator keys 34 provided for a user to interact with the exchange system 1. In a preferred embodiment, the keys are "soft" keys that have no designation on the actual membrane of the key 34, but rather are defined by software on the panel 10 directly above the actual key 34. The key definition will change based on the state of the system 1 at that time. The key 34 may be back lit and the intensity of the key back light varies along with intensity of the back light of the display 54. In addition to the three visible keys, two invisible keys are available for entry into service and nurse's menus, for example.

The display 54 is further provided for communication with the user. The display 54, in a preferred embodiment, has 302×240 pixels in a graphics mode and 40×30 characters in a text mode. Text and graphics may, however, be overlaid for greater flexibility. The display 54 may be back lit by a cold cathode fluorescent tube (CCFT), the intensity of which is variable under software control. The contrast is also variable under software control.

The alarm 56 and audio system is provided for audible feedback to the patient. Every press of the keys 34 results in a short audible tone. Any user set-up errors that are detected will result in a distinctive tone to prompt the user to look at the display 54 for instructions on correcting the set-up error. The service menu and the nurse's menu are accessed by holding down certain key combinations at the time of power-up. Access to these menus is not possible at any other time.

Figure 9:
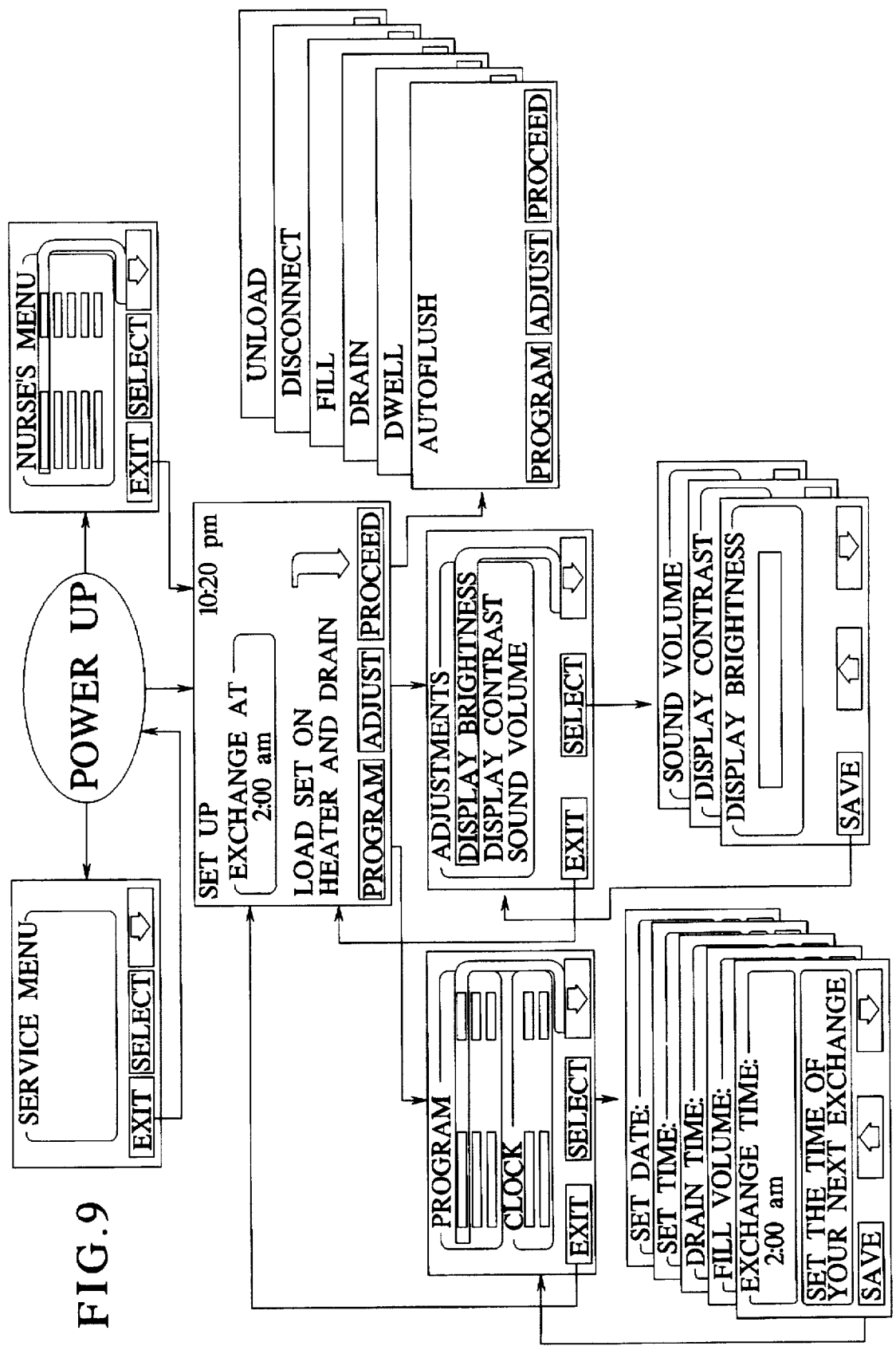
FIG. 9 illustrates perspective views of various user interface screens displayed by an embodiment of the system of the present invention.

FIG. 9 illustrates an overview of the user interface screens for the display 54. The orientation of the soft keys is also shown with their variable designations defined by the software of the system 1.

The scale 14 of the exchange system 1 in the drain tray 30 includes force sensing resistors (not shown). Force applied to the resistors causes the resistance to change. The more force applied, the lower the resistance becomes. If the force sensing resistors are placed in a simple voltage divider circuit, a certain force gives a repeatable voltage from the divider. The four sensing resistors can then be calibrated by running the system through an entire range of force and recording the corresponding voltage. Using the set of calibration voltages, the force on the force sensing resistors can be determined for all subsequent runs. Of course, other known scales may be implemented to measure the rate of the drain bag 20 on the drain tray 30.

The insulated heater 12 within the pouch 26 may include internal sensors (not shown) to monitor the temperature of the foil heater assembly. The internal sensors can be tested for accuracy in linearity by applying power to the heater element and monitoring the response of the sensors. Due to intrinsic properties of the nickel iron material of the element and the sensors, as the temperature increases, so does their resistances. If the sensor is placed in a bridge circuit, the change in resistance can be directly related to a change in voltage. The sensors are special traces etched onto the heater at the same time and of the same material as the heater trace itself. The sensor is a thin equivalent of the heater trace causing its resistance to be higher. When temperature increases, the resistance of the trace increases. The increase is detected by a bridge circuit which amplifies the change.

The exchange system 1, therefore, provides a simple, convenient and cost-effective device for providing an additional exchange during the night time. The system 1 satisfies a need for patients who require a fifth CAPD exchange or patients who desire a more convenient method of performing four exchanges. The system 1 is portable and performs an exchange using a twin bag using an extension line. The system 1 has two automated valves, ensures drain before fill and provides a simple user interface and an insulated heater to raise and maintain fluid temperature.

Although the present invention has been described with reference to a peritoneal dialysis procedure, it should be understood that the present invention is adaptable to other fluid control systems, such as intravenous feeding.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A system for controlling fluid flow, the system comprising:

a holder capable of holding a first container having a first solution therein;

a processor unit having an integral pump connected to the holder wherein the pump is capable of pumping the first solution from the first container in the holder;

a tray capable of holding a second container wherein the pump is capable of pumping a second solution to the second container; and an arm connecting the holder to the processor unit wherein the arm includes a hinge at a point of connection to the processor unit such that the arm is rotatable with respect to the processor unit.

2. The system of claim 1 further comprising:

a heater incorporated in the holder capable of heating the first solution in the first container in the holder.

3. The system of claim 1 further comprising:

a scale incorporated in the tray capable of weighing the second container placed on the tray.

4. The system of claim 1 wherein the means for controlling flow includes a fill valve controlling flow of the first solution from the first container.

5. The system of claim 1 wherein the means for controlling flow includes a drain valve controlling flow of the second solution to the second container.

6. The system of claim 1 further comprising:

an arm connecting the processor unit to the tray.

7. The system of claim 1 further comprising:

a display operatively connected to the processor unit.

8. The system of claim 1 further comprising:

an input means operatively connected to the processor unit.

9. The system of claim 1 further comprising:

means for effecting a structural relationship between the holder and the processor unit.

10. The system of claim 1 further comprising:

a cover connected to the holder to substantially enclose the first container in the holder.

11. The system of claim 1 further comprising:

a power switch operatively connected to the tray to activate the system.

12. The system of claim 1 further comprising:

means to alter position of the processor unit.

13. The system of claim 1 further comprising:

means to release the holder, the processor unit and the tray to orient in a non-operable position.

14. The system of claim 1 further comprising:

an audible means operatively connected to the processor unit capable of producing an audible signal.

15. The system of claim 1 further comprising:

an auxiliary processor in the tray operatively connected to the processor unit.

16. The system of claim 1 further comprising:

a real time clock operatively connected to the processor unit.

17. The system of claim 1 further comprising:

programmable timing means operatively connected to the processor unit to control activation of the system.

18. The system of claim 1 further comprising:

operator-actuated keys to control programming of the processor unit.

19. The system of claim 18 wherein the operator-actuated keys are modifiable by the processor unit.

20. The system of claim 1 wherein the means for controlling flow is a pneumatic pump.

21. The system of claim 1 further comprising:

sensing means for detecting temperature of the first solution in the container.

22. The system of claim 1 further comprising:

a plurality of strain gauges constructed and arranged with the tray capable of measuring weight of the second container on the tray.

23. A method for controlling fluid flow, the method comprising the steps of:

providing a holder capable of holding a first container having a first solution therein without hanging the first container;

providing a tray capable of holding a second container having a second solution therein without hanging the second container, the first container remotely situated from the second container;

controlling pumping of the solution from the first container and pumping of the second solution to the second container; and folding the holder and the tray into a second position not suitable for use wherein a first arm is connected to a second arm by a hinge wherein the first arm and the second arm are rotatable with respect to each other at the hinge.

24. The method of claim 23 further comprising the step of:

weighing the second solution in the second container without removing the second container.

25. The method of claim 23 further comprising the step of:

heating the first solution in the holder.

26. The method of claim 23 further comprising the step of:

selectively enclosing the first container in the holder.

27. The method of claim 23 further comprising the step of:

sensing temperature of the first solution in the first container.

28. The method of claim 23 further comprising the step of:

controlling draining of the first container and the filling of the second container.

29. The method of claim 23 further comprising the step of:

draining the first container only after weighing the second container.

30. The method of claim 23 further comprising the step of:

providing a display indicative of performed functions.

31. The method of claim 23 further comprising the step of:

providing a cover to selectively enclose the first container in the holder.

32. The method of claim 23 wherein the control of flow is performed by pneumatic pumping.

33. A portable peritoneal dialysis exchange system comprising:

a drain tray capable of holding a drain bag without hanging the drain bag;

a pouch capable of holding a solution bag without hanging the solution bag;

a collapsible linkage connecting the drain tray to the pouch; and a processor with a pumping means operatively connected to the drain bag and the solution bag to automate pumping of fluid to the drain bag from a patient and from the solution bag to the patient wherein the collapsible linkage includes a first arm extending between the pouch and the processor and a second arm extending between the processor and the drain tray wherein a hinge connects the first arm to the second arm and further allows each arm to rotate at the hinge.

34. The system of claim 33 further comprising:

a scale incorporated in the drain tray to measure weight of the drain bag.

35. The system of claim 33 further comprising:

a heating means incorporated in the pouch to effect heating of the solution bag and its contents.

36. The system of claim 33 wherein the pouch is insulated.

37. The system of claim 33 further comprising:

valves associated with the processor to assist the flow control means to control flow of fluids.

38. The system of claim 33 wherein the processor is constructed and arranged between the drain tray and the pouch, the pouch gravitationally feeding fluid from the solution bag toward the processor.

39. The system of claim 33 further comprising:

a display associated with the processor displaying functions of the processor.

40. The system of claim 33 further comprising:

keys associated with the processor to control programmable functions of the processor.

41. The system of claim 33 further comprising:

a cover constructed and arranged to selectively open and close the pouch.

42. The system of claim 33 further comprising:

means for adjusting orientation of the processor without affecting the orientation of the pouch.

43. The system of claim 33 further comprising:

a handle constructed and arranged on the linkage to selectively effect collapse of the linkage.

44. A system for controlling fluid flow, the system comprising:

a holder capable of holding a first container having a first solution therein;

a processor unit having an integral pump connected to the holder wherein the pump is capable of pumping the first solution from the first container in the holder;

a tray capable of holding a second container wherein the pump is capable of pumping a second solution to the second container; and a cover connected to the holder to substantially enclose the first container in the holder.

45. A system for controlling fluid flow, the system comprising:

a holder capable of holding a first container having a first solution therein;

a processor unit having an integral pump connected to the holder wherein the pump is capable of pumping the first solution from the first container in the holder and further wherein the pump is pneumatic; and a tray capable of holding a second container wherein the pump is capable of pumping a second solution to the second container.

46. A method for controlling fluid flow, the method comprising the steps of:

providing a holder capable of holding a first container having a first solution therein without hanging the first container;

providing a tray capable of holding a second container having a second solution therein without hanging the second container, the first container remotely situated from the second container;

controlling pumping of the solution from the first container and pumping of the second solution to the second container;

selectively enclosing the first container in the holder.

47. A method for controlling fluid flow, the method comprising the steps of:

providing a holder capable of holding a first container having a first solution therein without hanging the first container;

providing a tray capable of holding a second container having a second solution therein without hanging the second container, the first container remotely situated from the second container;

controlling pumping of the solution from the first container and pumping of the second solution to the second container; and providing a cover to selectively enclose the first container in the holder.

48. A method for controlling fluid flow, the method comprising the steps of:

provided a holder capable of holding a first container having a first solution therein without hanging the first container;

providing a tray capable of holding a second container having a second solution therein without hanging the second container, the first container remotely situated from the second container; and controlling pumping of the solution from the first container and pumping of the second solution to the second container wherein the pumping is performed pneumatically.

49. A portable peritoneal dialysis exchange system comprising:

a drain tray capable of holding a drain bag without hanging the drain bag;

a pouch capable of holding a solution bag without hanging the solution bag;

a collapsible linkage connecting the drain tray to the pouch; and a processor with a pumping means operatively connected to the drain bag and the solution bag to automate pumping of fluid to the drain bag from a patient and from the solution bag to the patient; and a cover constructed and arranged to selectively open and close the pouch.

* * * * *

UNITED STATES PATENT AND TRADEMARK OFFICE
CERTIFICATE OF CORRECTION

PATENT NO. : 5,782,796
DATED : July 21, 1998
INVENTOR(S) : Shahid Din, et al.

It is certified that error appears in the above-identified patent and that said Letters Patent is hereby corrected as shown below:

Column 6, Line 4: delete "16a" (2nd occ.) and insert --16b--

Column 6, Line 13: delete "16a" and insert --16b--

Column 6, Line 16: delete "16a" and insert --16b--

Column 6, Line 42: delete "16a" and insert --16b--

Column 6, Line 51: delete "16a" and insert --16b--

Column 7, Line 11: delete "16a" and insert --16b--

Column 7, Line 15: delete "16a" and insert --16b--

Signed and Sealed this

Fifteenth Day of June, 1999

Attest:

Attesting Officer

Q. TODD DICKINSON

Acting Commissioner of Patents and Trademarks